US006796942B1

United States Patent
Kreiner et al.

(10) Patent No.: US 6,796,942 B1
(45) Date of Patent: Sep. 28, 2004

(54) DEVICE FOR MEASURING PHYSICAL QUANTITIES, ESPECIALLY FOR MEASURING PRESSURE IN THE EYE

(75) Inventors: Christine Kreiner, München (DE); Volker Bödecker, Hannover (DE); Uwe Schnakenberg, Aachen (DE); Stella Marianne Ullerich, Aachen (DE); Peter Walter, Hürth (DE)

(73) Assignees: Acritec Gesellschaft fur Ophthalmologische Produkte mbH (DE); Mesotec Gesellschaft fur Medizinische Sensortechnik mbH (DE)

(*) Notice: Subject to any disclaimer, the term of this patent is extended or adjusted under 35 U.S.C. 154(b) by 193 days.

(21) Appl. No.: 10/089,363
(22) PCT Filed: Sep. 22, 2000
(86) PCT No.: PCT/EP00/09301
§ 371 (c)(1), (2), (4) Date: Jul. 23, 2002
(87) PCT Pub. No.: WO01/21063
PCT Pub. Date: Mar. 29, 2001

(30) Foreign Application Priority Data

Sep. 24, 1999 (DE) .......................................... 199 45 879

(51) Int. Cl.$^7$ ................................................. A61B 3/16
(52) U.S. Cl. ...................................................... 600/398
(58) Field of Search ........................... 600/398; 623/6.11

(56) References Cited

U.S. PATENT DOCUMENTS

| 4,816,031 A | 3/1989 | Pfoff |
| 5,005,577 A | 4/1991 | Frenkel |

FOREIGN PATENT DOCUMENTS

| DE | 19728069 | 2/1999 |
| DE | 19858172 | 6/2000 |
| EP | 0908756 | 4/1999 |

OTHER PUBLICATIONS

R. Puers, "Capacitive Sensors: When and How to Use Them", *Sensors and Actuators A*, CH, Elsevier Sequioa S.A., Lausanne, vol. A37/38, Jun. 1, 1993, pp. 93–105.

*Primary Examiner*—Eric F. Winakur
(74) *Attorney, Agent, or Firm*—Ostrolenk, Faber, Gerb & Soffen, LLP

(57) ABSTRACT

The invention relates to a device for measuring physical quantities in the eye, especially for measuring the intraocular pressure. The inventive device comprises a foldable telemetry system containing a coil (1) which is flatly arranged on a foldable support. Said coil is completely embedded in the biocompatible implant material together with an electronic mobile (4) that contains the electronic of the telemetry system.

18 Claims, 3 Drawing Sheets

DEVICE FOR MEASURING PHYSICAL QUANTITIES, ESPECIALLY FOR MEASURING PRESSURE IN THE EYE

The invention relates to a device according to the preamble of patent claim 1, as known from DE 197 28 069 C1.

PRIOR ART

The known device is used for measuring the intraocular pressure and comprises a foldable implant on which, outside the field of vision of the eye, there is a telemetry system having a pressure sensor and a transmitter device with coil. With the transmitter device, information corresponding to the sensor signals can be fed wirelessly to a receiver device arranged outside the eye. The received information is converted into reproducible data in an evaluation device connected to the receiver device.

In the known device, the telemetry system which can be implanted in the eye can have a data logger in which the measurement data delivered continuously from the pressure sensor can be stored and from which the measurement data can, when necessary, be retrieved for a limited time in transmit-receive mode.

OBJECT OF THE INVENTION

The object of the invention is to make available a device of the type mentioned above which can be folded or rolled and has excellent receive and transmit quality.

According to the invention, this object is achieved by the characterizing features of patent claim 1, the subclaims defining advantageous developments of the invention.

In the invention, the coil is arranged flat on a foldable support, in particular a support film, in the form of a plurality of adjacent coil windings in one plane surface. The telemetry device containing the electronics and/or the sensor are preferably contained in at least one electronic module (chip) and likewise applied with electrical contact to the coil on the foldable support. This arrangement is embedded in a foldable biocompatible implant material, in particular of polyorganosiloxane, e.g. polydimethylsiloxane. Here, the implant material can be used not only as a covering for the transmitter device and telemetry device, but also as a transmission medium to the sensor for the physical quantity to be measured, which especially can be the intraocular pressure or the temperature in the eye. That is to say, in a preferred embodiment, the sensor is also surrounded by the biocompatible implant material. However, it is also possible to leave the sensor uncovered on a sensor surface, which is sensitive to the physical quantity to be measured or recorded, or in a defined sensor area. The physical quantity to be measured and present in the eye, for example the intraocular pressure or temperature, then acts directly on the sensor surface or this sensor area. For the physical quantity, it is also possible to use a transmission medium other than the implant material.

By means of the planar configuration of the coil with a plurality of mutually adjacent coil windings which preferably lies in a plane perpendicular to the optic axis of the eye or of the implant designed as intraocular lens, a high transmit and receive quality is obtained without impairing the foldability or rollability of the implant material. Moreover, the necessary compatibility with the eye is achieved for the whole device. In addition to one planar layer, it is also possible for a plurality of planar layers (planes) lying one above the other to be provided for the coil windings.

In a preferred manner, the implant is designed, as an intraocular lens, the telemetry device and the transmitter device with the coil being accommodated outside the optic lens part, in particular mainly in the area of the haptic part of the intraocular lens surrounding the optic part of the lens. For this purpose, the haptic part can have an annular area which surrounds the optic lens part and within which the planar arrangement of the coil windings is accommodated. The coil windings are preferably designed as planar electrical conductor tracks which are preferably made of precious metal, especially gold. The conductor tracks of the coil windings are produced on the support film using conventional planar technology, for example by metal deposition, in particular electrodeposition, as are known in microstructuring processes.

The implant can also be of annular design. The coil windings are then arranged on at least one of the ring surfaces. The annular implant is preferably fixed on the sulcus of the eye. The ring can be made partly of a hard material, in particular PMMA, and partly of a flexible material, in particular silicone. The implant is preferably covered with a biocompatible material, for example silicone rubber. The ring can also be made entirely of silicone, in which case a stabilizing haptic part made in particular of PMMA or of another rigid material is provided.

The support film is designed as a thin flexible and foldable film which ensures a good adhesion for the metal of the coil windings, and in particular the film material has dielectric properties and can be made of a suitable plastic, e.g. a polyimide.

On account of the high degree to which the device can be rolled or folded, it can be implanted in the eye without having to modify the usual techniques of minimally invasive surgery. In this way, microelectronic and sensoric components can be fitted in the eye for wireless energy and signal transmission, for example in the form of an artificial intraocular lens which is foldable. The intraocular lens unfolds after implantation.

EXAMPLES

The invention is explained in more detail on the basis of an illustrative embodiment and with reference to the figures, in which.

Figure 1:
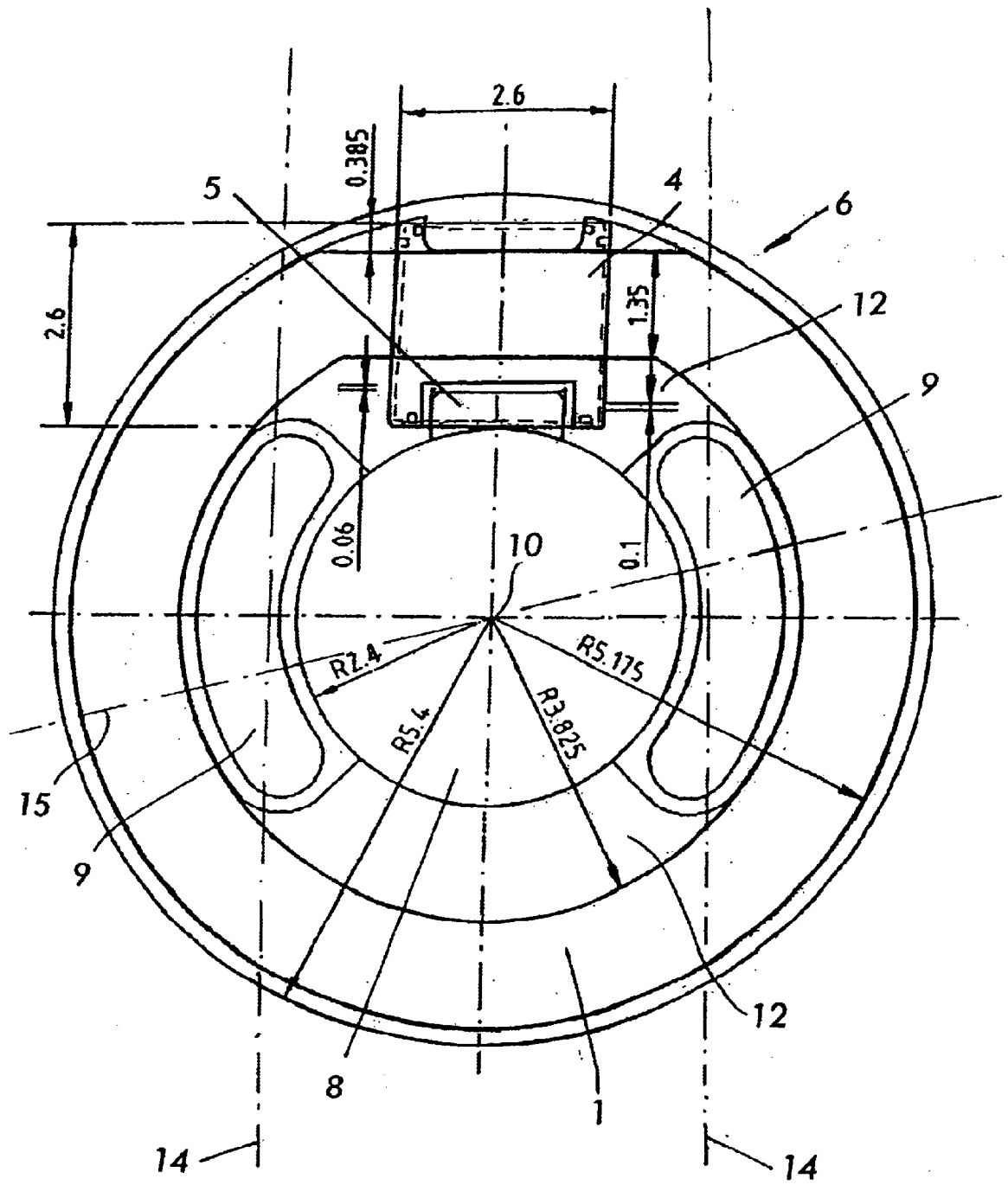
FIG. 1 shows a plan view of an illustrative embodiment designed as an intraocular lens.

The illustrative embodiment of an eye implant 6 shown is designed as an intraocular lens. The latter has an optic lens part 1 which can be fitted in the visual field of the eye. The optic lens part a has an optic axis 10 which is substantially perpendicular to the plane of the drawing in FIG. 1. In the implanted state, the optic axis is oriented substantially on the visual axis of the eye. The optic lens part 8 substantially covers the visual field of the eye.

Situated on an annular support which is designed as a support film (FIG. 2) and which is flexible, i.e. can be folded and rolled, there is a coil 1 which forms the inductance in the transmit-receive device. The coil is made up of planar coil windings 3 in the form of conductor tracks lying adjacent to one another. The conductor tracks of the coil windings 3 lie next to one another in a plane which is substantially perpendicular to the optic axis 10. The width of a coil winding is of the order of ca. 3 to 90 μm, preferably ca. 10 to 90 μm. About 10 to 65 coil windings can be provided in a particular plane for the coil 1. By means of such a design of the coil 1, the ability of the support film 2 to be folded, rolled and, where appropriate, bent remains unimpaired. The coil windings 3 can be produced, for example, by electro-deposition, as is known in microstructuring processes. In the illustrative embodiment shown, the coil 1 is situated on a circular surface. However, to adapt it to the site of use of the implant 6, the coil can also be made oval or oval-like or can have another configuration.

Figure 3:
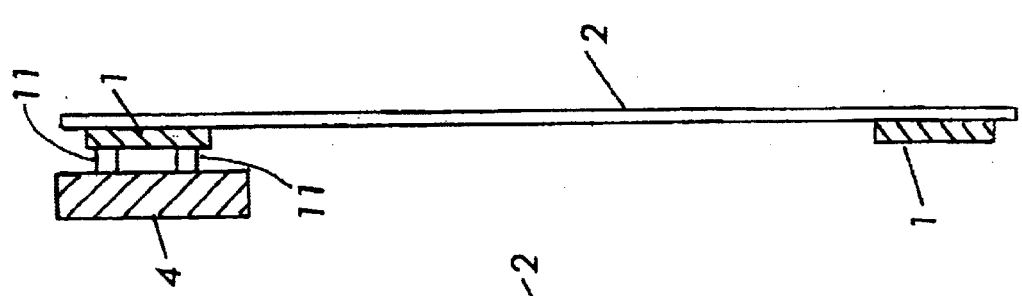
FIG. 3 shows a sectional representation of the telemetry system represented in FIG. 2.

The electronics of the telemetry system, accommodated in an electronic module (chip) 4, are also situated on the support film 2, it being possible of course to use a plurality of electronic modules. A sensor 5 for recording the physical quantity to be measured, in particular the intraocular pressure, can preferably be provided in an edge area on this electronic module 4. As FIG. 3 shows, the electronic module 4 is suitably contacted with the coil 1 (electrical contacts 11). In the area of the electronic module 4, in order to make contacting easier, the coil windings 3 preferably extend in a substantially rectilinear manner, as is shown in a rectilinear area of windings 7 in FIG. 2. The electrical contact 11 between the coil 1 and the electronic module 4 can be obtained in hybrid technology or flip-chip technology by bonding. The electrical contact points 11 (FIG. 3) can be formed by gold bumps with a thickness of 30 μm and less. In addition to a monolithic structure, the chip or the electronic modules can be incorporated in one or more films and are thus able to be folded and rolled.

The planar coil windings have a thickness (height) in the region of 5 to 60 μm. The height of the electronic module 4 is ca. 600 μm and can be substantially less than for example 300 μm. The surface of the electronic module 4 is ca. 2.0 mm×2.0 mm. The thickness of the support film can be about 8 μm. The coil can have an external radius of ca. 5.15 mm and an internal radius of ca. 3.85 mm. The area of the support film 2 lying to the inside of the coil 1 can be punched out so that the support film 2 is present as an annular support film which is substantially covered with the coil windings 3.

Figure 4:
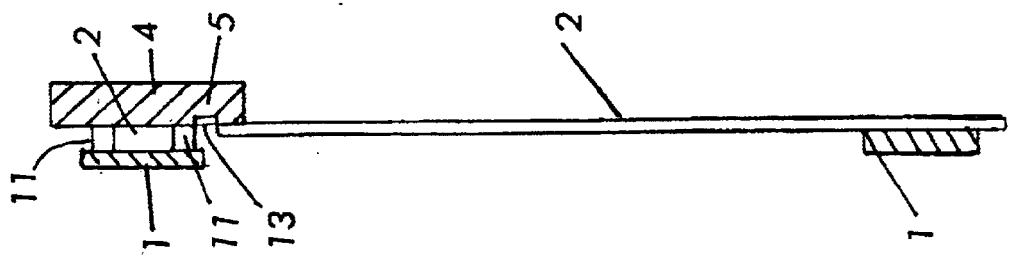
FIG. 4 shows a sectional representation of a telemetry system in a further illustrative embodiment.
Figure 2:
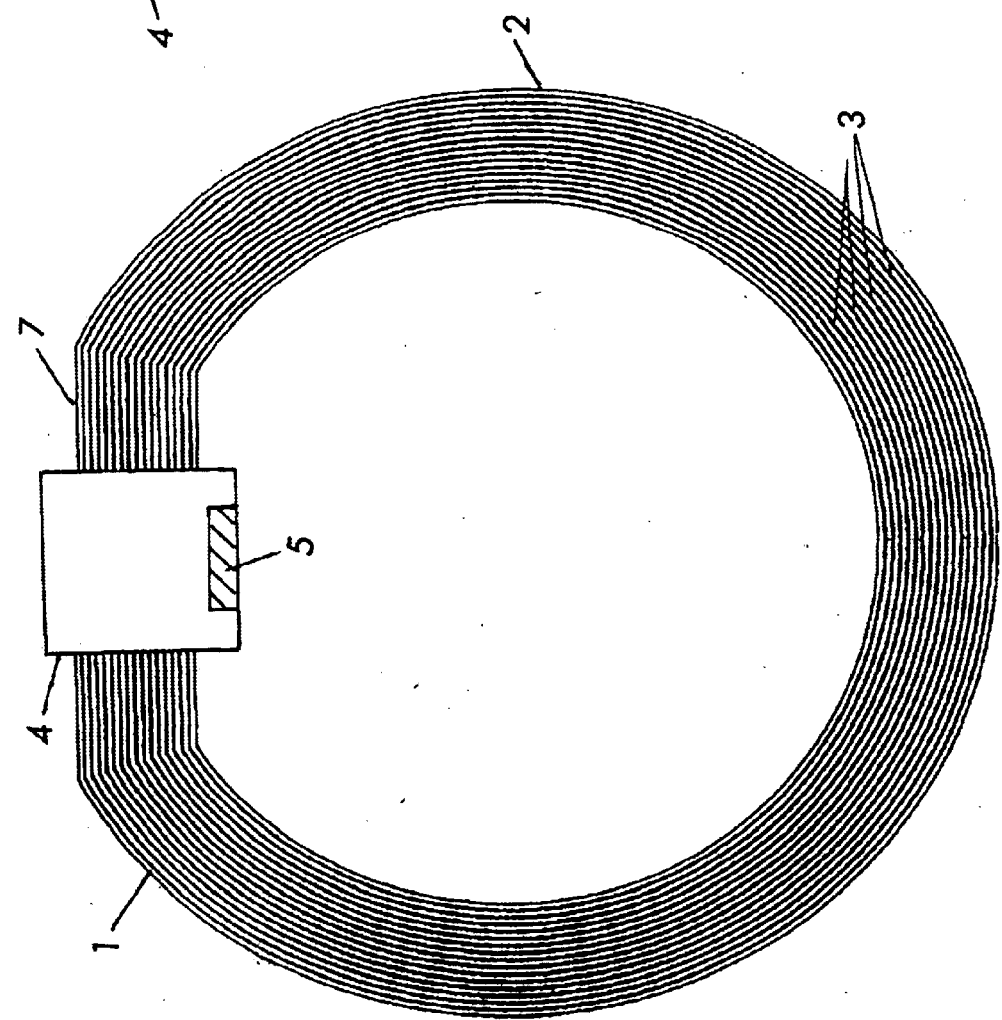
FIG. 2 shows a plan view of an embodiment of a telemetry system which can be used in the illustrative embodiment represented in FIG. 1.

The support film 2 with the telemetry devices arranged thereon, as shown in FIGS. 2 and 3, is covered completely, in particular by embedding, with a biocompatible implant material, in particular lens material. The implant material or lens material also covers the sensor 5 which is designed in particular as a pressure sensor. FIG. 1 shows the intraocular lens into which the telemetry system shown in FIGS. 2 to 4 is embedded. The dimensions indicated in FIG. 1 are illustrative and can be varied within the limits permitted for implantation in the eye.

As can be seen from FIG. 1, the coil 1 is situated within an annular haptic area which concentrically surrounds the optic lens part 8. This can be a circular ring or an oval or oval-like ring. An annular area 12 of the lens material lying between this annular haptic area and the optic lens part 8 is provided with oblong holes 9 which, at their border edges, extend approximately concentrically about the optic axis 10 with respect to the annular coil 1 and the annular area 12. These oblong holes 9 not only facilitate the folding or rolling of the lens, but also aid the fixing of the lens in the eye since ocular tissue can grow into these oblong holes. As can also be seen from FIG. 1, the sensor 5 is situated in proximity to the optic lens part 8. It lies between the optic lens part 8 and the inner edge of the coil 1 in an area which does not overlap the surface of the coil 1. The sensor 5 is enclosed by a lens material which is situated between two ends of the oblong holes 9 in the annular area 12 of the lens material. The lens material serves to transmit the physical quantity to be measured in the eye, for example the temperature or the intraocular pressure. A polyorgano-siloxane, in particular polydimethylsiloxane, is preferably used for the lens material. It is also possible to provide another transmission medium in the area of the sensor 5 or of a sensor area responding to the physical quantity (e.g. pressure, temperature) or to leave this area uncovered, as will be explained below with reference to FIG. 4.

The external diameter of the intraocular lens can be about 12 mm or less, e.g. 8.5 mm. The diameter of the optic lens part 8 can be 6 mm or less, for example 4.8 mm. The thickness of the lens in the center of the optic lens part 8 can be about 0.780 mm or less. In the nonoptic area, the thickness can be 0.500 mm or less, but in the area of the electronic module 4 it must be ensured that this is completely enclosed by the lens material and, accordingly, the lens in this area has a corresponding thickness. The length of the oblong holes 9 can be about 4.6 mm or less. The width can be 1.2 mm or less.

In the illustrative embodiment shown in FIG. 3, the coil 1 and the electronic module 4 are situated on the same side of the support film 2. In the illustrative embodiment shown in FIG. 4, the coil 1 is situated on one side of the support film 2 and the electronic module 4 on the other side of the support film 2. The electrical contacting 11 between the coil 1 and the electronic module 4 is effected with the aid of contacts through the support film 2.

As can be seen from the illustrative embodiment in FIG. 4, an area of the sensor 5 sensitive to the physical quantity to be measured can be left uncovered. In the illustrative embodiment shown, this is a sensor surface 13. For this purpose, a cutout can be provided in the support film 2. This cutout is also situated in the covering implant or intraocular lens material. However, it is also possible to use, in the cutout, a material transmitting the physical quantity which is different than the implant material. In the illustrative embodiment shown in FIG. 4, the exposed sensor surface 13 is situated on the inside of the sensor 5. The exposed sensor surface can also lie on the other side, i.e. on the outside of the sensor 5.

As can be seen from FIG. 1, the implant or lens material can be folded or rolled about fold edges 14 which extend approximately parallel to one another and lie on both sides of the electronic module 4. Even if the electronic module 4 is made of a nonfoldable monolithic module, it is still possible to obtain a considerable reduction in the implant cross section for implantation. The two fold edges 14 extend on both sides of the electronic module. The implant can also be folded along a fold edge 15 which extends through the lens center (optic axis 10). It will be apparent from this that the implant has a large number of folding possibilities, even when the electronic module 4 is of monolithic design. By means of the special design of the coil 1, the latter can be folded while obtaining a high inductance.

A memory can be provided in the electronic module 4, which memory stores the pressure values continuously recorded by the sensor, in particular the pressure sensor 5.

These pressure values can be retrieved from this memory from time to time, for example at weekly intervals, and transmitted from the telemetry device to a receiver device (not detailed) with attached evaluation device, as is described for example in German patent specification DE 197 28 069 C1. It is also possible for the electronic module 4 to be formed from foldable support material, so that a deformation of the intraocular lens to a small diameter is possible and only a small incision needs to be made in the eye for the implantation. The lens material is designed in such a way that it unfolds after implantation and adopts the desired lens shape.

Figure 5:
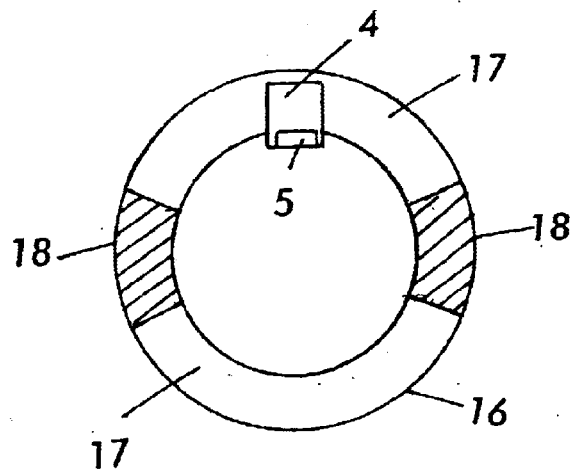
FIG. 5 shows an illustrative embodiment of an annular implant.
Figure 6:
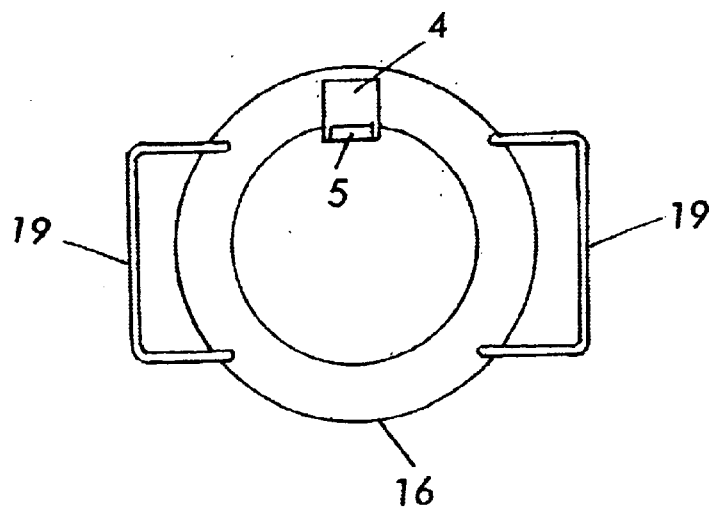
FIG. 6 shows a further illustrative embodiment of an annular implant with closed haptic loops.
Figure 7:
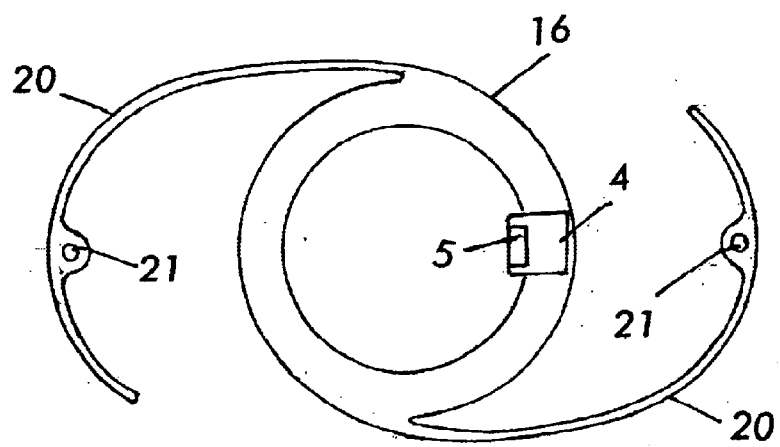
FIG. 7 shows an illustrative embodiment of an annular implant with open haptic loops.

In the illustrative embodiments shown in FIGS. 5 to 7, an implant body 16 is designed in an annular shape. The cutout provided in the inside of the ring is dimensioned at least so that it lies outside the field of vision when the annular implant is arranged in the eye. The coil (not shown) is designed in the manner shown in FIG. 2. It is situated on one or both surfaces of the annular implant. The attachment of the sensor 5 and of the electronic module 4 is effected in the same way as has been explained in the previous illustrative embodiments. The sensor 5 is situated inside the annular arrangement of the coil 1, as can be seen from FIG. 2.

In the illustrative embodiment shown in FIG. 5, the annular implant 16 is made of hard or rigid ring parts 17, preferably of PMMA, and flexible ring parts 18, in particular of silicone. By this means, it is possible to fold the annular implant 16 about a fold axis routed through the flexible ring parts 18. The external diameter of the ring is about 12 to 15 mm. The width of the ring can be 1 to 3 mm.

In the illustrative embodiment shown in FIG. 6, the annular implant body 16 has closed haptic loops 19. The illustrative embodiment shown in FIG. 7 has open haptic loops 20. The annular implant bodies 16 of illustrative embodiments 6 and 7 are preferably made of silicone rubber. The haptic loops 19 and 20 are preferably made of a rigid material, in particular PMMA. In the illustrative embodiment shown in FIG. 7, fixation holes 21 are provided in the open haptic loops 20. This ensures a stable positioning of the implant body 16 in the eye. The illustrative embodiments in FIGS. 5 to 7 are suitable for fixation in the sulcus of the eye. If appropriate, additional fixation holes (not shown) can also be provided in the illustrative embodiment in FIG. 5.

The illustrative embodiments in FIGS. 5, 6 and 7 can be completely covered with an envelope of silicone rubber or with another biocompatible envelope. The intraocular pressure is transmitted to the sensor surface of the pressure sensor 5 via this resilient envelope. The envelope material forms the transmission medium for transmitting the intraocular pressure to the sensor surface of the sensor 5.

Thus, in all of the illustrative embodiments, it is possible to achieve a complete covering of the implant with biocompatible material and a perfect transmission of pressure to the sensor surface of the sensor 5 via the envelope material.

| [List of reference numbers] | |
| --- | --- |
| 1 | coil |
| 2 | support film |
| 3 | coil windings |
| 4 | electronic module (chip) |
| 5 | sensor, in particular pressure sensor |
| 6 | implant, in particular intraocular lens |
| 7 | rectilinear area of windings |
| 8 | optic lens part |
| 9 | oblong hole |
| 10 | optic axis |
| 11 | electrical contact |
| 12 | annular area |
| 13 | sensor surface |
| 14 | fold edge |
| 15 | fold edge |
| 16 | annular implant body |
| 17 | rigid ring part |
| 18 | flexible ring part |
| 19 | closed haptic loop |
| 20 | open haptic loop |
| 21 | fixation hole |

What is claimed is:

1. A device for measuring physical quantities in the eye, with a foldable implant on which, arranged outside an implant part covering the field of vision the eye, there is a telemetry device having a sensor and having a transmitter device with coil for wireless transmission of infonmation corresponding to the sensor signals, and with a receiver device which is arranged outside the eye receives the information sent by the transmitter device, and with an evaluation device which converts the received information into reproducible data, characterized by further comprising an arrangement comprising, on an annular foldable support, the coil is arranged in the form of a plurality of adjacent coil windings in at least one surface, and at least one electronic module containing the electronics of the telemetry device is electrically contacted with the coil, and in that the arrangement is embedded in the foldable biocompatible implant material.

2. The device as claimed in claim 1, characterized in that the coil windings are formed from planar electrical conductor tracks.

3. The device as claimed in claim 1, characterized in that the coil windings are arranged in one or more planes.

4. The device as claimed in claim 1, characterized in that the sensor is covered completely or partially by a transmission medium transmitting the physical quantity.

5. The device as claimed in claim 4, characterized in that the biocompatible material with which the device is covered forms the transmission medium.

6. The device as claimed in claim 1, characterized in that the coil windings in the area of their connection to the electronic module extend in a substantially rectilinear manner.

7. The device as claimed in claim 1, characterized in that the coil windings extend substantially in the entire implant part lying outside the field of vision of the eye.

8. The device as claimed in claim 1, characterized in that the sensor is designed as a pressure sensor.

9. The device as claimed in claim 8, characterized in that the pressure sensor continuously measures the intraocular pressure, and the electronics of the telemetry device have a memory in which the sensor signals are stored for a temporally limited transmission to a receiver device.

10. The device as claimed in claim 1, characterized in that the sensor lies outside the field of vision of the eye in an area which does not overlap the surface of the coil windings.

11. The device as claimed in claim 1, characterized in that the sensor lies inside the ring formed by the coil.

12. The device as claimed in claim 1, characterized in that the implant is designed as an intraocular lens, and in that the annular support in the area of the optic lens part has a cutout which lies inside the coil windings.

13. The device as claimed in claim 1, characterized in that oblong holes are formed in the implant material between the coil and the implant part lying in the field of vision.

14. The device as claimed in claim 13, characterized in that the sensor (5) lies in an annular area (12) of the implant material in which the oblong holes (9) extend.

15. The device as claimed in claim 1, characterized in that the at least one surface in which the coil is arranged extends approximately perpendicular to an optic axis of the implant.

16. The device as claimed in claim 1, characterized in that the coil is arranged on one surface and the electronic module on the other surface of the annular support.

17. The device as claimed in claim 1, characterized by an annular implant body made of at least partially flexible material which forms the support for the coil.

18. The device as claimed in claim 17, characterized in that the annular implant body can be fixed in the sulcus of the eye.

* * * * *